United States Patent [19]

Denen

[11] Patent Number: 5,070,878

[45] Date of Patent: * Dec. 10, 1991

[54] DETECTOR AND LOCALIZER FOR LOW ENERGY RADIATION EMISSIONS

[75] Inventor: Dennis J. Denen, Columbus, Ohio

[73] Assignee: Neoprobe Corporation, Columbus, Ohio

[*] Notice: The portion of the term of this patent subsequent to Jan. 31, 2006 has been disclaimed.

[21] Appl. No.: 404,403

[22] Filed: Sep. 8, 1989

Related U.S. Application Data

[63] Continuation-in-part of Ser. No. 271,023, Nov. 14, 1988, abandoned, and a continuation-in-part of Ser. No. 248,920, Sep. 23, 1988, Pat. No. 4,893,013, which is a continuation-in-part of Ser. No. 27,197, Mar. 17, 1987, Pat. No. 4,801,803.

[51] Int. Cl.$^5$ .......................... A61B 5/00; G01T 1/161
[52] U.S. Cl. ................................. 128/659; 250/336.1; 250/370.01; 250/370.13
[58] Field of Search ................... 128/653 R, 654, 659; 250/370.01, 370.07, 370.12, 370.13, 336.1

[56] References Cited

U.S. PATENT DOCUMENTS

| 3,427,454 | 2/1969 | Webb | 128/659 |
| 3,638,022 | 1/1972 | Kozlov | 250/370.01 |
| 3,646,407 | 2/1972 | Meuleman | 250/370.01 |
| 3,999,071 | 12/1976 | Siffert et al. | 250/370.13 |
| 4,461,952 | 7/1984 | Allemand et al. | 250/370.7 |
| 4,682,895 | 7/1987 | Costello | 128/636 |
| 4,801,803 | 1/1989 | Denen et al. | 250/336.1 |
| 4,893,013 | 1/1990 | Denen et al. | 128/659 |

FOREIGN PATENT DOCUMENTS 2117900 10/1983 United Kingdom ............. 250/336.1

OTHER PUBLICATIONS

P. J. O'Dwyer et al., "Intraoperative Probe-Directed Immunodetection Using a Monoclonal Antibody", Archives of Surgery, vol. 121 (Dec. 1986), pp. 1391-1394.
D. T. Martin et al., "Intraoperative Radioimmunodetection of Colorectal Tumor with a Hand-Held Radiation Detector", American Journal of Surgery, vol. 150, No. 6 (Dec. 6, 1985), pp. 672-675.
D. R. Aitken et al., "Portable Gamma Probe for Radioimmune Localization of Experimental Colon Tumor Xenografts" Journal of Biological Research, vol. 36, No. 5 (1984), pp. 480-489.
E. W. Martin, Jr., et al., "Radioimmunoguided Surgery: Intraoperative Use of Monoclonal Antibody 17-1A in Colorectal Cancer", Hybridoma, vol. 5, Supplement 1 (1986), pp. S97-S108.
Richard D. Baxter, "Miniature Hybrid Preamplifier for CdTe Detectors". IEEE Transactions of Nuclear Science, vol NS-23, No. 1 (Feb. 1976), pp. 493-497.
IEEE Transaction on Nuclear Science, vol. NS-23, No. 1, Feb. 1976, pp. 594-598, New York, US: D. A. Garcia et al.: "Thrombus Detection Using I-125-Fibrinogen and a cdTe Probe", *p. 594, 'Instrumentation'; figures*.

(List continued on next page.)

Primary Examiner—Kyle L. Howell
Assistant Examiner—Krista M. Pfaffle
Attorney, Agent, or Firm—Mueller and Smith

[57] ABSTRACT

A detector particularly suited for use in immuno-guided surgery capable of detecting very faint gamma emissions and thereby localizing cancerous tumor. The detector employs a hand manipular probe within which is contained a crystal such as cadmium telluride which is secured in a light-tight environment. A noise immune structuring of the probe and crystal combination includes the utilization of electrically conductive, compliant cushion layer located at one face of the crystal in conjunction with freely abutting biasing and ground contacts. A nylon, resilient retainer is positioned in tension over the assemblage of crystal, ground and biasing contacts and compliant layers to achieve a compressively retained assemblage. A dead air space is developed between the forward facing window of the probe and the crystal retaining assemblage.

40 Claims, 5 Drawing Sheets

OTHER PUBLICATIONS

Journal of Nuclear Medicine, vol. 26, No. 1, Jan. 1985, pp. 85-87, New York, US; L. Davis et al.: "Data Acquisition using a Scintillation Detector Interfaced to a Personal Microcomputer", *Whole article*.

Kerntichnic, vol. 19, No. 9.10, Sep./Oct. 1977, pp. 424-427, Berlin, DE; K. Matauschek et al.: "The Semiconductor Detector Probe 72030, with the RFT Radiation Measuring Unit 20026, for the Diagnosis of Intraocular Tumors", *p. 425, 'Design to Execution of the Probe 72030'; p. 426, The Preamplifier; figures*.

IEEE Nuclear Science, vol. 27, No. 1, Feb. 1980, pp. 496-502, IEEE, New York, US; H. B. Barber et al.: "Small Radiation Detectors for Bronchoscopic Tumor Localization": pp. 496, 497; Figures.

Bigu et al., "Passive Radon/Thoron Personal Dosimeter Using an Electrostatic Collector and a Diffused-Junction Detector", Rev. Sci. Instr. 56(1), Jan. 1985, pp. 146-153.

Zanio et al., "Analysis of CdTe Probes", IEEE Trans. Nucl. Sci. (USA), vol. N-S 19, No. 3 (Jun. 1972), pp. 257-262.

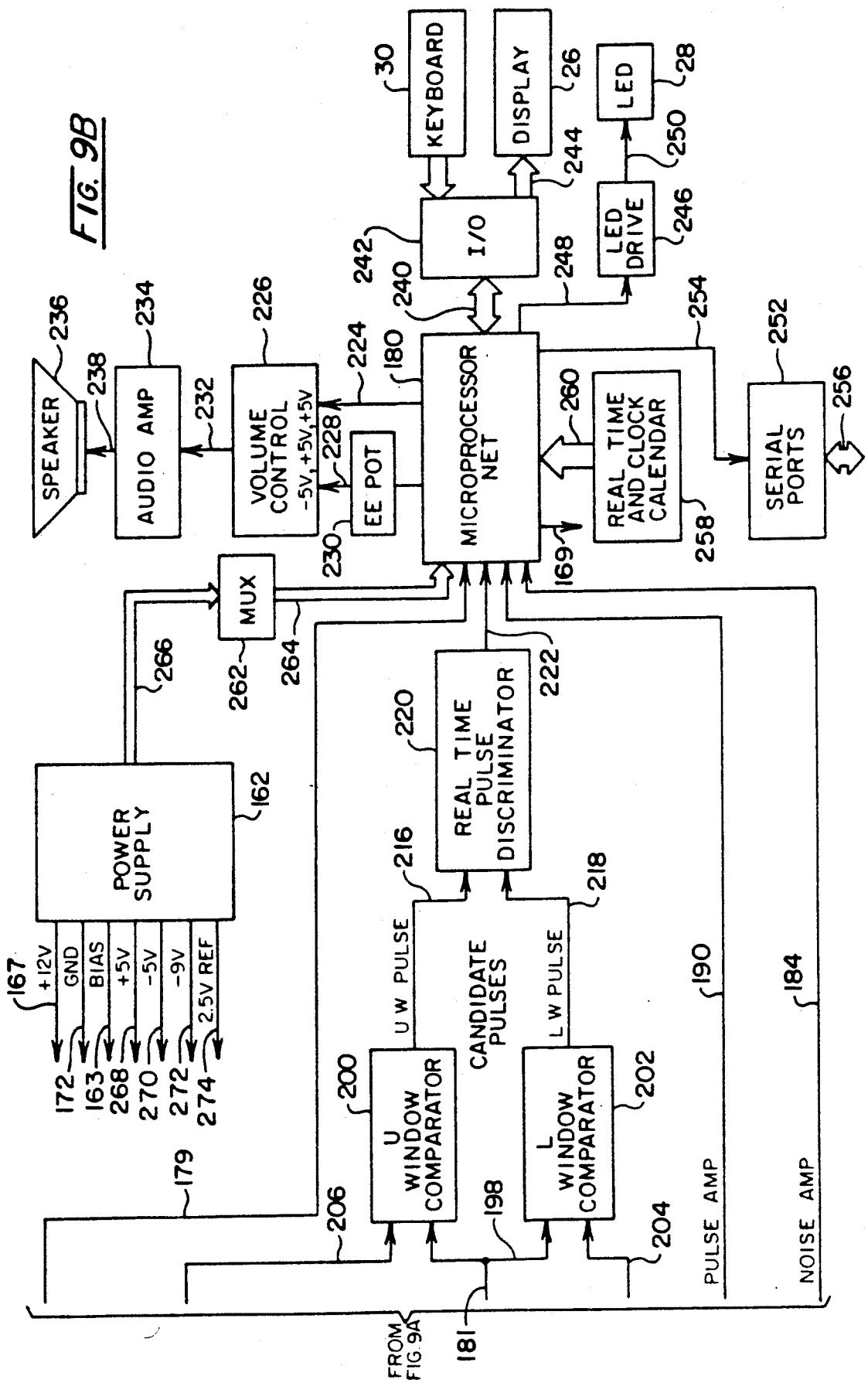

DETECTOR AND LOCALIZER FOR LOW ENERGY RADIATION EMISSIONS

CROSS REFERENCE TO RELATED APPLICATION

This application is a continuation-in-part of application Ser. No. 07/271,023, filed Nov. 14, 1988, "Detector and Localizer for Low Energy Radiation Emissions, by Denen, et al., now abandoned, and is a continuation-in-part of application Ser. No. 248,920, filed Sept. 23, 1988, now U.S. Pat. No. 4,893,013, which is a continuation-in-part of application Ser. No. 027,197, field Mar. 17, 1987, now U.S. Pat. No. 4,801,803, all of the aforesaid applications and patents being assigned in common herewith.

BACKGROUND

The detection and treatment of cancerous tissue has been the subject of intense investigation for many years. One among the many approaches to its detection has concerned the identification of tumor specific antigens. Where these antigens can be identified, radionucleid labeled antibodies have been employed which tend to collect at tumor sites. When so concentrated, somewhat elaborate radiation detection equipment then is employed to record, for example, by imaging the concentrations of the emissive substances and thus to locate neoplastic tissue. Important advances in this procedure have been evidenced through the use of monoclonal antibodies or fragments thereof with a variety of radionucleides. Typical techniques for carrying out imaging of these antibodies have involved, for example, tomographic scanning, immunoscinitigraphy and the like. The particular choice of radionucleid for labeling antibodies is dependent upon its nuclear properties, the physical half life, the detection instrument capabilities, the pharmacokinetics of the radiolabeled antibody, and the degree of difficulty of the labeling procedure. The most widely used of these radionucleides in nuclear medicine imaging include technetium, $^{99m}$Tc, iodine $^{125}$I, $^{131}$I, and indium, $^{111}$In. Of the above, for localizing tumors of the gastro-intestinal tract, the radionucleid $^{131}$I is used as the marker or label in conjunction with imaging gamma cameras and the like which are relative large and elabroate devices positioned above the patient during the imaging process.

In spite of its somewhat extensive utilization, $^{131}$I is not an ideal radionucleid for use in diagnositc medicine. The high energy gamma-photon emitted from $^{131}$I is poorly detected by the classic gamma camera and like instrumentation. In addition, the administered marker emissions deliver a high radiation dose to the patient. Further, the imaging definition of these external imaging devices has not been satisfactory for many reasons. As tumor sites become smaller, the radionucleid concentration thereat will tend to be lost, from an imaging standpoint, in the background or blood pool radiation necessarily present in the patient.

Over the recent past, a surgical procedure has been developed concerning the differentiation and removal of such neoplastic tissue through the use of much lower energy gamma emission levels for example, $^{125}$I(27-35 kev). While such a radiolabel cannot be employed with conventional external imaging or scanning devices because the radiation is strongly absorbed by the tissue intermediate between the tumor and the surface of the patient's body, it has been found that when employed with a probe type detection structure, a highly effective differentiation technique can be evolved. More particularly, the longer half like of this type of radiolabel coupled with a surgical methodology involving the waiting of appropriate intervals from the time of introduction of the radiolabelled antibody to the patient to the time of surgery, can evolve a highly accurate differentiation of cancerous tumor. This improved method of localization, differentiation and removal of cancerous tumor involves a surgical procedure wherein the patient suspected of containing neoplastic tissue is administered an effective amount of an antibody specific for neoplastic tissue which is labeled with a radioactive isotope as above-noted exhibiting photon emissions of specific energy levels. Next, the surgical procedure is delayed for a time interval following such administration for permitting the labeled antibody to preferentially concentrate in any neoplastic tissue present in the patient, as well as to be cleared from normal tissue so as to increase the ratio of photon emissions from the neoplastic tissue to the background photon emissions. Thereafter, an operative field of the patient is surgically accessed and tissue within the operative field to be examined for neoplastic tissue has the background photon emission count determined. Once the background photon emission count for the tissue within the operative field has been determined, this hand-held probe is manually positioned within the operative field adjacent tissue suspected of being neoplastic. Readouts then can be achieved from probe counting for differentiation. In the above regard, reference is made to the following technical publications:

I. "CEA-Directed Second-Look Surgery in the Asymptomatic Patient after Primary Resection of Colorectal Carcinoma", E. W. Martin, Jr., MD, J. P. Minton, MD, PhD, Larry C. Carey, MD. *Annals of Surgery* 202:1 (Sept. 1985 301-12.

II. "Intraoperative Probe-Directed Immunodetection Using a Monoclonal Antibody", P. J. O'Dwyer, MD, C. M. Mojzsik, RN MS G. H. Hinkle, RPh, MS, M. Rousseau, J. Olsen, MD, S. E. Tuttle, MD, R. F. Barth, PhD, M.O. Thurston, PhD D. P. McCabe, MD, W. B. Farrar, MD, E. W. Martin, Jr., MD. *Archives of Surgery* 121 (Dec. 1986) 1321-1394.

III. "Intraoperative Radioimmunodetection of Colorectal Tumors with a Hand-Held Radiation Detector", D. T. Martin, MD, G. H. Hinkle, MS RPh, S. Tuttle MD, J. Olsen, MD, H. Abdel-Nabi, MD, D. Houschens, PhD, M. Thurston, PhD, E. W. Martin, Jr., MD, *American Journal of Surgery,* 150:6 (Dec. 1985) 672-75.

IV. "Portable Gamma Probe for Radioimmune Localization of Experimental Colon Tumor Xenografts", D. R. Aitken, MD, M. O. Thurston, PhD, G. H. Hinkle, MS RPh, D. T. Martin, MD, D. E. Haagensen, Jr., MD, PhD, D. Houchens, PhD, S. E. Tuttle, MD E. W. Martin, Jr., MD. *Journal of Surgical Research,* 36:5 (1984) 480-489.

V. "Radioimmunoguided Surgery: Intraoperative Use of Monoclonal Antibody 17-1A in Colorectal Cancer". E. W. Martin, Jr., MD, S. E. Tuttle, MD, M. Rousseau, C. M. Mojzisik, RN MS, P. J. O'Dwyer, MD, G. H. Hinkle, MS RPh, E. A. Miller, R. A. Goodwin, O. A. Oredipe, MA, R. F. Barth, MD, J. O. Olsen, MD, D. Houchens, PhD, S. D. Jewell, MS, D. M. Bucci, BS, D. Adams, Z. Steplewski, M. O. Thurston, PhD, *Hybridoma,* 5 Suppl 1 (1986) S97-108.

Reference further is made to commonly assigned U.S. Pat. No. 4,782,840, entitled "Method for Locating, Differentiating, and Removing Neoplasms" by Edward W. Martin Jr., and Marlin O. Thurston, issued Nov. 8, 1988.

The success of this highly effective differentiation and localization technique is predicated upon the availability of a probe-type detecting device capable of detecting extremely low amounts of radiation necessarily developed with the procedure. In this regard, low energy radionucleides are used such as $^{125}I$ and the distribution of radiolabeled antibody with the nucleid is quite sparse so that background emissions can be minimized and the ratio of tumor-specific counts received to background counts can be maximized. Conventional radiation detection probe-type devices are ineffective for this purpose. Generally, because a detection device is required for the probes which is capable of performing at room temperatures, a very fragile or delicate detection crystal such as cadmium telluride is employed. The probe using such a crystal must be capable of detecting as little as a single gamma ray emission which may, for example, create electron-hole pairs in the crystal of between about 2,000 and 4,000 electrons. Considering that an ampere generates $6.25 \times 10^{18}$ electrons per second, one may observe that extremely small currents must be detectable with such a probe. However, the probe system also must be capable of discriminating such currents from any of a wide variety of electrical disturbances, for example which may be occasioned from cosmic inputs, room temperature molecular generated noise, and capacitively or piezoelectrically induced noise developed from the mere manipulation of the probe itself. While being capable of performing under these extreme criteria, the same probe further must be capable of performing under the requirements of the surgical theater. In this regard, it must be secure from ingress of contaminants; it must be sterilizable; and it must be rugged enough to withstand manipulation by the surgeon within the operating room environment. Further, the system with which the probe is employed, must be capable of perceptively apprising the surgeon of when neoplastic tissue is being approached such that the device may be employed for the purpose of guiding the surgeon to the situs of cancer. Additionally, for surgical use, the probe instrument must be small, so as to be effectively manipulated through surgical openings and the like. Such diminutive size is not easily achieved under the above operational criteria. This technique has been described as "radioimmuno-guided surgery", a surgical approach developed by E. W. Martin, Jr., MD, and M. O. Thurston, PhD.

In addition to the capability of performing under the above-noted relatively extreme criteria, the probe instrument called upon for the instant use preferably should be fabricable employing practical manufacturing techniques. One approach to improving the fabricability of the probe instruments is described in application for U.S. patent Ser. No. 07/248,920 by Denen, et al., entitled "Detector and Localizer for Low Energy Radiation Emissions", filed Sept. 23, 1988, now U.S. Pat. No. 4,893,013, issued Jan. 9, 1990. The probe structuring disclosed therein is one wherein necessary ground and bias are applied to opposite sides of the gamma detecting crystal utilizing electrodes which are fixed to the crystal face. An elastomeric retainer is used to structurally retain all the components together including the crystal, the biasing arrangement, and the like. While successful production has been achieved with the structure so described, the technique described therein is one requiring the use of a multi-component cap for the assembly and one wherein deterioration has been noted in the coupling of the bias and grounding electrodes to the radiation responsive crystals. Further improvements in the structure of the probe have been deemed necessary both in terms of the integrity of the association of external components with the gamma radiation crystal as well as in conjunction with the ease of fabricability of the probe.

SUMMARY

The present invention is addressed to apparatus for detecting and locating sources of emitted radiation and, particularly, sources of gamma radiation as well as the method of fabricating such apparatus. Detection is achieved under room temperature conditions using a crystal such as cadmium telluride and with respect to very low energy emissions. To achieve the extreme sensitivity capabilities of the apparatus, an instrumentation approach has been developed in which the somewhat fragile crystal is securely retained in isolation from externally induced incidents otherwise creating excessive noise. In this regard, microphonic effects are minimized through employment of a sequence of materials exhibiting divergent acoustic impedances. Capacitive or piezoelectric effects occasioned by the most minute of intercomponent movements are controlled to acceptable levels. Compressive retention of the crystal and electrical contacts with it is employed in conjunction with electrically conductive but pliable surface supports. The instrument also achieves performance while being structured for assembly by practical manufacturing techniques.

A feature of the invention provides an instrument for detecting and locating sources of radiation emissions having predetermined energy levels which includes a housing having a forwardly disposed portion. A crystal mount is presented which is positioned within the housing forwardly disposed portion and which is formed of materials attenuating radiation of the predetermined energy levels and which has a forwardly disposed, crystal receiving cavity extending inwardly thereinto from a forwardly disposed receiving cavity extending inwardly thereinto from a forwardly disposed opening. A resilient electrically insulative polymeric layer is positioned within the cavity and a radiation responsive crystal is located within the cavity which has a rearwardly disposed surface positioned facing the electrically insulative layer and has a side portion extending to a forwardly disposed surface. A biasing arrangement extends within the cavity to provide a bias contact adjacent the electrically insulative layer and a first electrically conductive compliant member which is conformable with and in contacting adjacency between the crystal rearwardly disposed surface and the bias contact is provided. A second electrically conductive compliant member which is conformable with and in contacting adjacency with the crystal forwardly disposed surface is provided and a grounding arrangement is positioned in abutting adjacency with the second compliant member for electrically grounding the crystal forwardly disposed surface. A resilient retainer is positioned in tension over the grounding arrangement and the crystal forwardly disposed surface for compressively retaining components including the ground and the second compliant member against the crystal forwardly disposed surface and the rearwardly disposed surface of the crystal against the first compliant member, the bias contract and the polymeric layer to an extent effective to provide a stabilization of the electrical contacts to the crystal derived from the biasing arrangement and the grounding arrangement and to retain the components in a statically stable state. A forward cover is positioned to enclose the crystal mount, crystal receiving cavity, the crystal, the grounding arrangement, and the resilient retainers for permitting transmission of the radiation emission of predetermined energy levels.

Another feature of the invention provides an instrument for detecting sources of radiation emissions which includes a housing having a forwardly disposed portion. A crystal mount is positioned within the housing forwardly disposed portion having an electrically insulative forwardly disposed crystal supporting surface. A radiation responsive crystal having a rearwardly disposed surface is positioned facing the crystal mount crystal supporting surface and has a side portion extending to a forwardly disposed surface. Further, an electrical bias arrangement having a bias contact at the crystal mount crystal supporting surface is provided as well as a first electrically conductive compliant cushioning member conformable with and in contacting adjacency between the crystal rearwardly disposed surface and the bias contact. A second electrically conductive compliant cushioning member is conformable with and in contacting adjacency with the crystal forwardly disposed surface and a grounding arrangement is positioned in adjacency with the second compliant member for electrically grounding the crystal forwardly disposed surface. A resilient retainer arrangement is positioned in tension over the second electrically conductive compliant cushion member for compressively retaining the second electrically conductive compliant cushioning member upon the crystal mount supporting surface and a forward cover is positioned over and in enclosing relationship with the crystal mount, the crystal supporting surface, the crystal and the first and second electrically compliant cushioning members for excluding external contaminants, and having a forwardly disposed window portion surface, formed of material permitting substantial transmission of the radiation emission to the crystal forwardly disposed surface, the window portion being spaced forwardly from the crystal to define a dead air space for enhancing the acoustic isolation of the crystal.

As another feature, the invention provides an instrument for detecting sources of gamma radiation emissions which includes a housing having a forwardly disposed portion. A crystal mount is positioned within the housing forwardly disposed portion having an electrically insulative forwardly disposed crystal supporting surface. A gamma radiation responsive crystal having a rearwardly disposed surface is positioned facing the crystal mount crystal supporting surface and has a side surface extending to a forwardly disposed surface. A compliant cushioning arrangement for locating the crystal upon the crystal supporting surface with substantial immunity from externally induced vibration phenomena is provided and electrical biasing is provided for applying an electrical bias to the crystal rearwardly disposed surface. Similarly, a grounding arrangement is provided for electrically grounding the crystal forwardly disposed surface. A resilient retainer arrangement is positioned in tension over the gamma radiation responsive crystal, the compliant cushioning arrangement, the electrical biasing arrangement, and the grounding arrangement for effecting the retention thereof in compression upon the crystal mount crystal supporting surface. Finally, a forward cover is positioned over and in enclosing relationship with the crystal mount crystal supporting surface, the crystal, the compliant cushioning arrangement, and the grounding arrangement for excluding external contaminants and is seen to have a forwardly disposed window portion formed of material permitting substantial transmission of gamma radiation to the crystal forwardly disposed surface. The window portion is spaced forwardly from the crystal to define a space enhancing the isolation of the crystal from externally induced vibration phenomena.

Other objects of the invention will, in part, be obvious and will, in part, appear hereinafter.

The invention accordingly, comprises the apparatus possessing the construction, combination of elements, and arrangement of parts which are exemplified in the following detailed disclosure. For a fuller understanding of the nature and objects of the invention, reference should be had to the following detailed description taken in connection with the accompanying drawings.

BRIEF DESCRIPTION OF THE DRAWINGS

FIGS. 9A and 9B combine as labeled to form a block diagram of the functional components of the control system associated with the instrument of the invention.

DETAILED DESCRIPTION OF THE INVENTION

Figure 1:
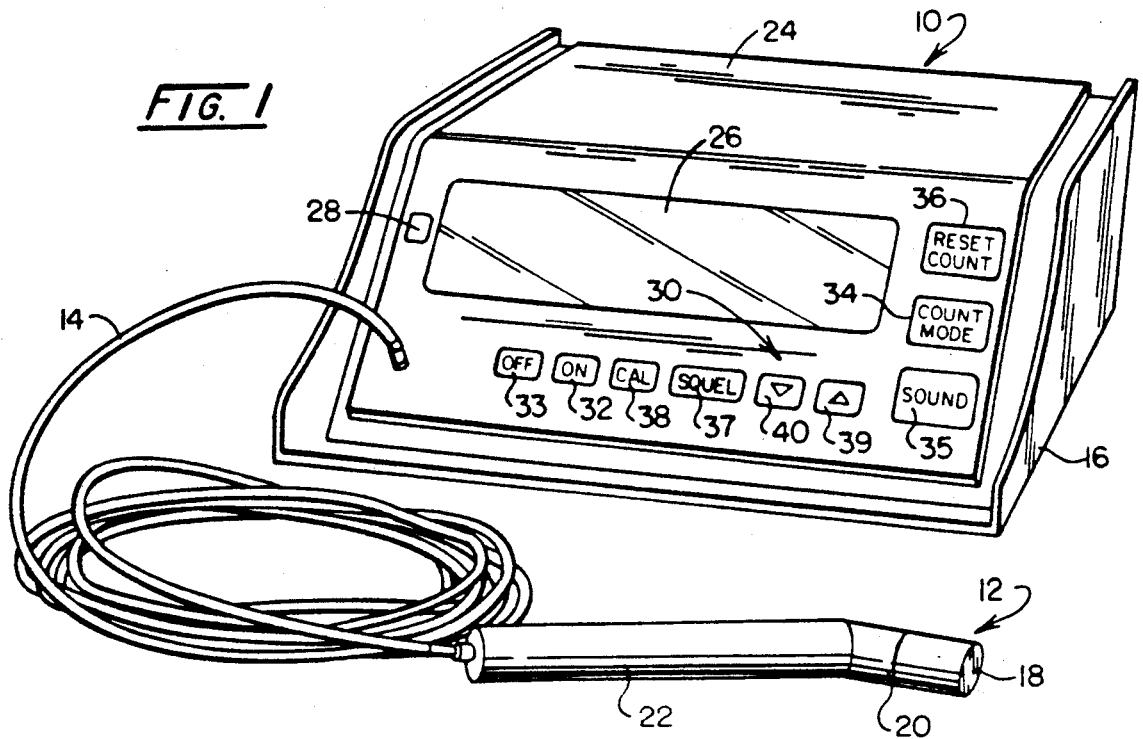
FIG. 1 is a perspective view of the probe instrument and associated console representing the instrumentation of the invention.

Referring to FIG. 1, an embodiment of the probe and supporting instrumentation of the invention particularly designed for employment in the medical-surgical field is represented generally at 10. This assemblage includes a hand-manipular probe represented generally at 12 which is coupled by a triaxial cable 14 to a console 16. The probe 12, which preferably is retained by the surgeon within a disposable polymeric sheath or cover is maneuvered about the region of surgical interest to locate tumerous tissue for resection. When used in conjunction with colonic surgery, for example, the probe 12 is maneuvered through a surgical opening in the body cavity and essentially brought into contact with organs under study by the surgeon. When employed in a radioimmuno-guided mode, a loudspeaker or annunciator within the console 16 may be activated to provide a "siren" form of output which apprises the surgeon that the probe 12 is at a site of cancer. Thus, it is necessary that the device 12 be of convenient length and comfortable to grasp. The probe 12 is seen to include a radiation acceptance surface or window 18 located at the tip of an angularly oriented portion thereof 20. Portion 20 extends from a hand-grippable portion 22 at an angle of about 30° to facilitate its maneuverability about the back or hidden side of organs and, preferably, is coated with a low-friction surface material such as TEFLON (polytetrafluoroethylene) to enhance noise avoidance otherwise occasioned by the rubbing of surface 18 over tissue and the like during surgery.

Because the assemblage 10 is used in a surgical theater, the console 16 also is readily cleaned, having a smooth, one-piece touch sensitive polymeric surface 24 surmounting a relatively large LCD readout or display 26, a dual colored LED readout 28 and a sequence of finger-actuated switches. These switches or keyboard, as represented generally at 30 permit the microprocessor driven console 16 to carry out an instructive or "user friendly" dialogue with the practitioner. For purpose of safety, the device is powered by a rechargeable battery.

In addition to conventional on and off switches shown, respectively, at 32 and 33, the switches provided on the console 16 include a count mode switch 34, a sound switch 35, a reset count switch 36, a squelch function switch 37, a calibration function switch 38, and up and down incrementing switches for adjustment within certain of the switch generated modes as shown, respectively, at 30 and 40.

The probe 12 must be capable of performing essentially at room temperature. Thus, the device employs a cadmium telluride crystal and, because of the preferred low energy levels of radiation which it is called upon to detect, must be capable of operatively reacting to low energy gamma ray interactions. The interaction of gamma rays with such crystals is primarily through three processes, namely the photo-electric effect, Compton scattering, and pair production. In the photo-electric effect, a photon of energy, hv, interacts with an atom as a whole. Its energy is completely transferred to an electron, usually in the innermost shell. The electron is ejected with a kinetic energy: $e_{kin} = hv - E_b$, where $E_b$ is the binding energy of the orbital electron, h is Planck's constant, and v is the frequency associated with the wave nature of the gamma radiation. Such electrons undergo many collisions until this energy is shared with some thousands of other electrons. Each of these electrons leaves behind a positively charged region called in the literature a "hole". At the energies of $^{125}I$ Compton scattering is of minor importance. Pair production refers to the reaction of an electron and a photon to the gamma ray. Since this process requires more than 1.0 Mev it does not occur in the present application. In Compton scattering, the primary photon may interact with any one of the orbital electrons. The electrons are considered essentially as free electrons under the condition that the primary photon energy is large compared with the electron binding energy. The interaction may be analyzed as the elastic collision between the primary photon and the electron. Energy is shared between the recoil electron and the secondary photon. This secondary photon travels in a direction different from that of the primary photon, and is referred to as the scattered photon.

Thus, as an incoming gamma ray is absorbed by the crystal, it transfers some or all of its energy to electrons, which as charged particles pass through the semiconductor producing electron-hole pairs and, therefore, the capability of charge-transfer within the crystal medium.

when a charge particle produces electron-hole pairs in the semiconductor, the electric field causes these charge carriers to move toward and accumulate at the appropriate electrodes. As these charges move toward or are collected at the electrodes, they induce a charger or electrical pulse signal in the circuit external to the detector. It is then necessary to pre-amplify these signals and feed them to the electronics of the control unit or console 16.

For effective performance, the probe 12 must be capable of generating and discerning signals representing gamma ray strikes which are of extremely low energy. In this regard, a gamma ray interaction with the cadmium telluride crystal may produce two to four thousand electrons. It being recognized that $6.25 \times 10^{18}$ electrons per second presents one ampere of current, the relative sensitivity of the instant device will become apparent. As a consequence, the mechanical structuring of the mounting arrangement for the crystal within the probe 12 is of critical importance as is the technique for detecting and treating these significantly small charges representing gamma ray interactions.

Figure 2:
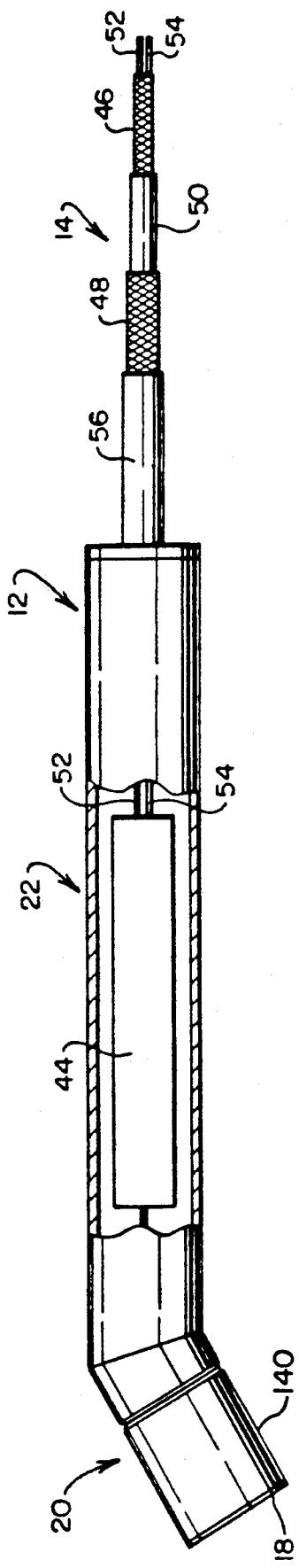
FIG. 2 is a side elevational view of the probe instrument shown in FIG. 1 with portions broken away to reveal internal structure.

Looking to FIG. 2, a more detailed representation of the probe device 12 is revealed. The angular orientation of the front portion 20 is shown having the noted 30° cant with respect to the central axis of the hand gripped portion 22. Device 12 is small having an overall length of about 19 cm and portion 22 having a length of about 12.7 cm. The overall diameter of the cylindrical structure 12 is about 1.9 cm. Experience to the present, utilizing low energy radiolabeling and achieving very high sensitivity on the part of the probe, for many applications has removed the need for supplementary forward collimation. The hand grip portion 22 carries a preamplifier on an elongate circuit board as represented in general at 44. Depending upon the energies of radiation encountered, the probe 12 housing is formed of an electrically conductive and thus shielding material which functions to attenuate radiation.

Cable 14 supplies power to the preamplifier to the probe, as well as bias and ground to the crystal and functions to transmit the preamplifier treated output signals. Cable 14 includes silver cladding components 46 and 48 which are mutually insulated and spaced by a polytetrafluoroethylene cover (TEFLON) 50 which is somewhat loose to permit flexure. The innermost leads, formed of TEFLON insulated silver, of the arrangement at respective lines 52 and 54 carry the output signals from the preamplifier 44 and a bias signal, for example 30 volts, for application to the rear face of the crystal within the device 12. Clad 46 carries a 12 volt power supply for the preamplifier circuit, while outer clad 48 carries ground for the system. An outer silicon rubber cover then is provided at 56.

Figure 3:
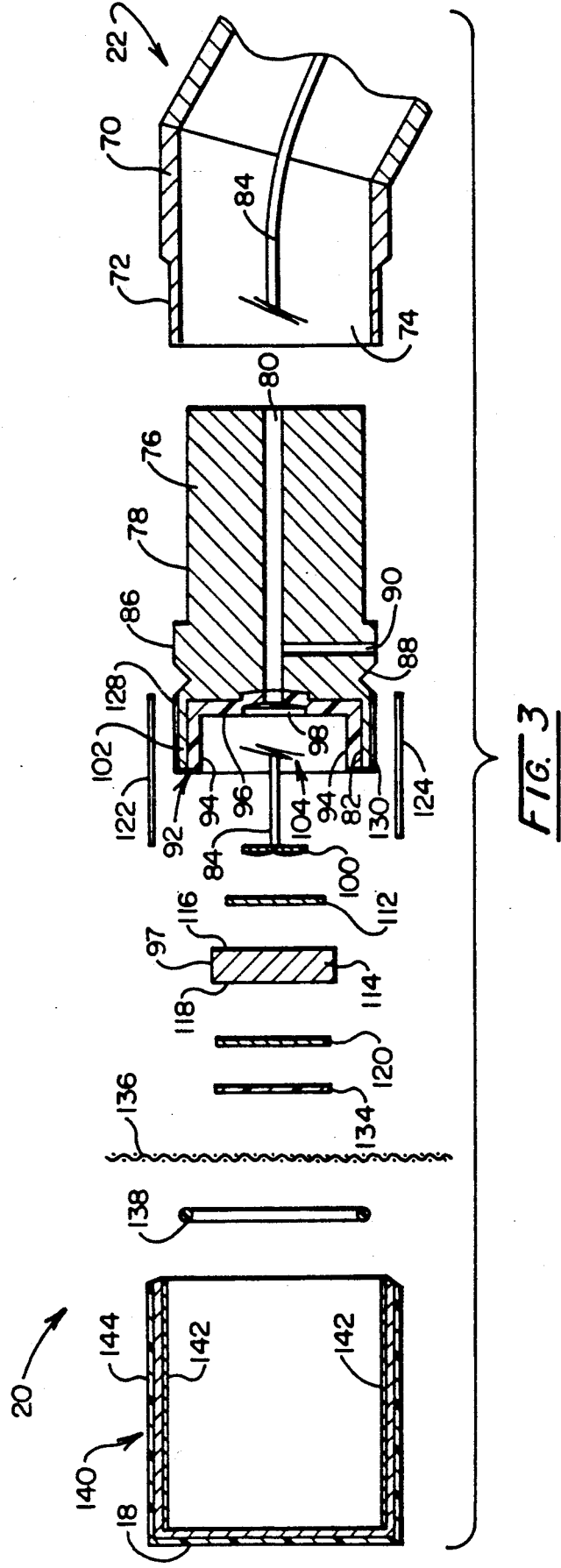
FIG. 3 is an exploded view of the forward assemblage of the instrument of FIG. 2.

Looking to FIG. 3, an exploded detail of the nose or forward portion 20 of probe 12 is provided. This portion 20 retains a radiation responsive crystal 114, formed preferably of admium telluride, in a light-tight and mechanically secure orientation while maintaining necessary ground and bias conditions upon it. Generally, such crystals as at 114 will have a rigidity or physical consistency somewhat similar to chalk and are formed having very light gold coatings on their surfaces. Thus, the mounting of such delicate crystals and their operation within a probe instrument as at 12 requires a highly refined design architecture. However, it is also important that the structure of the probe 12 be such as to permit its fabrication in a reasonably practical manner.

FIG. 3 shows the hand-graspable portion as at 22 extending to a supporting tubular portion 70. The forwardly disposed tubular region of portion 70 including its cylinder connector surface 72 are configured having an internal diameter defining a chamber 74. Chamber 74 receives a generally cylindrically shaped slug or crystal mount 76 along with a conductive epoxy retainer layer 146 (see FIG. 4) which retains the slug 76 in position.

Slug or crystal mount 76 is formed of a suitable radiation attenuating material such as lead and is of a general cylindrical configuration. In this regard, the rearwardly disposed cylindrical surface thereof 78 is configured for the notes slideable mounting within chamber 74 of the housing rearward portion 22. Extending centrally through slug 76 is an access opening 80 passing therethrough to a forwardly-disposed cylindrical recess represented generally at 82. Opening 80 functions to carry an insulated lead 84. Lead 84 functions as a bias-signal transmission wire leading to the physically adjacent preamplification stage circuit board 44 within the hand-graspable portion of the instrument at 22 (See FIG. 2). The cylindrical surface 78 of slug 76 is seen to terminate at a cylindrical collar region thereof 86 which is configured having an annular retainer groove 88 formed therein and which further incorporates a bore 90 extending in gas flow communication with the centrally disposed opening 80. Bore 90 serves to equalize gas pressure between the handle or hand graspable portion 22 of the instrument and the forwardly disposed components. The bore further functions to receive a tool for facilitating removal of the slug or crystal mount 76 and its associated assemblage of components for maintenance purposes and the like.

Within recess 82 there is formed, in situ an electrically insulative layer 92 which additionally functions as a cushioning mount for the cadmium telluride crystal 114 of the assemblage. Formed from a silicon rubber, the layer 92 is structured such that its external surface defines the walls of a crystal receiving cavity represented generally at 104, the side surfaces of which are depicted at 94 and the bottom surface of which is shown at 96. Additionally formed with this material is an annular depression 98 which is configured to receive a correspondingly configured bias contact member 100 formed at the terminus of insulated lead 84. Contact 100, for example, may be formed of an electrically conductive copper foil adhesively retained upon the leads within insulated lead 84. With the provision of the depression 98, the bias contact member 100 may be flush mounted along the bottom surface of the insulative layer which as noted may also serve to provide a cushioning effect. The sides 94 of the layer 92 defined cavity 104 are of a length for fully receiving the corresponding sides 97 of the crystal 114 to be mounted therein. Note that the radiation attenuating material of the crystal mount 76 at sides 102 forming recess 82 is coextensive with the side 94 of the cavity 104. This portion of the retainer 76 collar or shoulder 86 functions to block radiation otherwise incident on the sides of the crystal when it is positioned within the assemblage.

The widthwise extent of the cavity 104 across the inwardly disposed surfaces of sides 94 thereof is slightly greater than the corresponding widthwise extent of crystal 114. A spacing or gap 95 (FIG. 4) thus is formed between cavity sides 94 and the side surface 98 of crystal 114. For example, for a cylindrically shaped crystal as depicted, the cavity 104 is cylindrically shaped having a slightly greater outer diameter than the crystal. This small gap 95, for example 0.005 inch, serves to prevent noise phenomena resulting from any contact occurring between the side 97 of the crystal and the cavity 104 sides 94. Accordingly, gap 95 is formed having a width effective to avoid electrical noise phenomena which otherwise may be generated or occur as a consequence of contact between crystal side 97 and cavity side surface 94.

Figure 5:
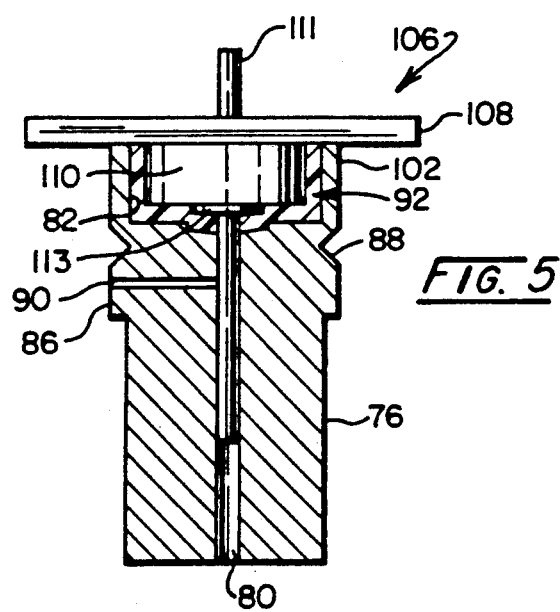
FIG. 5 is a partial sectional view showing a tooling arrangement for providing an electrically insulated layer within the cavity of a crystal retainer of the instrument of FIGS. 2 and 3.

Cavity 104 including side surfaces 94, bottom 96, and depression 98, preferably is formed with a tooling arrangement wherein its shape and dimensions are customized to the corresponding shape and dimension of the crystal assemblage to be inserted therein, taking into account the formation of gap 95. Looking to FIG. 5, a tooling arrangement for so customizing the cavity 104 by the process of molding layer 92 is revealed. The material used for layer 92 may, for example, be a silicon rubber identified as "Two-Part RTV" rubber marketed by Chembar, Inc., Groveport, OH 43125. This material is prepared by combining an HF RTV silastic material with a catalyst in accordance with a predetermined ratio. The material is poured within recess 82 of the crystal retainer 76 and a tool 106 which is comprised of a rectangular aligning bar 108, a male crystal mold 110, and a centrally-disposed aligning bar or rod 111 is inserted into the deposition. Note that rod 111 protrudes downwardly into opening 80 and that the mold 110 incorporates a cylindrical protrusion 113 functioning to form the earlier-described depression 98. In general, the silastic material is located about recess 82, whereupon the tool 106 is inserted for an interval sufficient to permit curing. The tool 106 then is withdrawn and the resultant silastic layer 92 is one which receives the crystal and related components to be positioned within with the spacing deriving gap 95. While providing electrical insulation, layer 92 also serves to contribute a cushioning function.

Returning to FIG. 3, upon positioning the bias contact member 100 as coupled with lead 84 within the depression 98 of layer surface 96, an annular of disk shaped electrically conductive compliant member 112 is positioned over the biasing contact 100 in freely-abuttable fashion. The compliant member 112 preferably is formed of a non-waven TEFLON cloth (stretched, highly crystalline, unsintered polytetrafluoroethylene) marked under the trade designation "GORETEX" having a thickness, for example, of about 0.020 in. and being filled with carbon particles to establish the requisite electrical conductivity. Component 112 not only functions to provide an intimate contact with biasing component 100, but, importantly, serves to establish a corresponding electrical contact with the radiation responsive crystal 114. The rearwardly disposed face 116 of crystal 114 freely abuts against the conforming surface of component 112 to develop an intimate and surface-conforming electrical contact. Additionally, the component 112 serves the important function of cushioning the delicate crystal 114.

Figure 6:
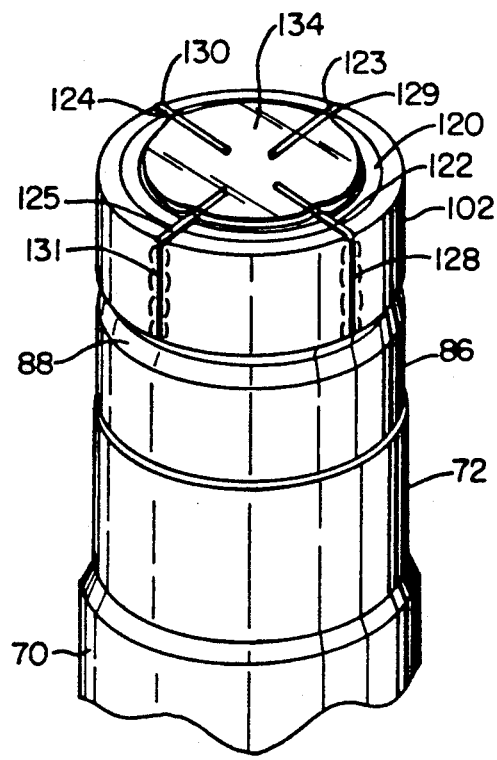
FIG. 6 is a perspective view showing the component assemblage of the instrument of FIGS. 2 and 3 which is developed during the fabrication thereof.

Ground potential is applied to the opposite or forwardly-disposed face 118 of crystal 114. This is carried out by positioning another conductive and compliant member 120, which may be configured identically as member 112, (carbon filled non-woven TEFLON) in freely abuttable fashion over surface 118. As before, the component 120 serves to provide a freely-abutting electrical contact through a conforming intimacy with surface 118. To establish a ground potential, four thin platinum wires 122-125 are provided which are swaged within respective grooves 128-131 formed within surface 102 of slug 76 as seen in FIG. 6. The wires 122-125 then are bent over as shown in FIG. 6 to contact the forwardly-disposed surface of compliant member 120. This sub-assembly is secured by a small disk 134 of transparent tape.

The small, thin platinum wires 122-125 establish an appropriate ground condition at the forward face 118 of crystal 114 through member 120 while imposing only a very minimal potential blockage of any impinging radiation. To enhance and stabilize the electrical contact both from wires 122-125 and the biasing contact member 100, the assemblage of disk 134, compliant disk 120, crystal 114, compliant disk 112, biasing contact 100, and layer 92 are retained in a compressive, physically or dynamically stable state by a resilient retainer 1356 which is positioned in tension over the noted assembly and retained in such tension by a conventional elastic O-ring 138 which engages the retainer 136 within groove 88 of crystal retainer or slug 76.

Figure 7:
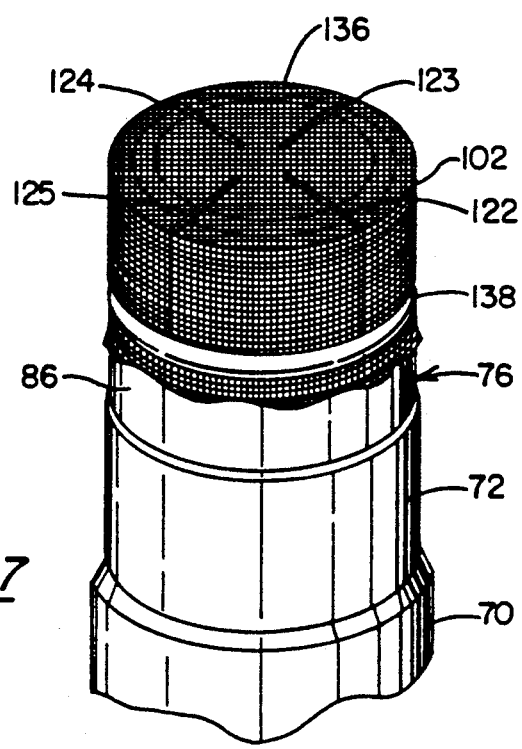
FIG. 7 is another perspective view of the instrument of FIGS. 2 and 3 showing a next step in the assembly procedure thereof.

Looking additionally to FIG. 7, the retainer 136 is represented as a resilient web which may be formed of nylon or the like. The web is positioned over the noted assemblage of components and drawn downwardly over them as well as over the outer surface 102 of retainer 76 to be retained in such tension by the O-ring 138. A simple cup-shaped jig may be employed for this purpose. The resultant assemblage has been found to both effect a stabilization of the electrical contacts for biasing and grounding purposes, and to retain all components in adjacency with crystal 114 in a desirably statically stable state to avoid the generation of motion induced noise.

Returning to FIG. 3, a forward cover 140 is positioned over the above-described assemblage as it is installed within housing chamber 74. Because of the extension of the radiation shielding material, such as lead, of retainer 76 about the sides of crystal 114 by virtue of the side portions 102, the forward cover 140 may be made entirely and unitarily of a convenient radiation transmissive material such as aluminum. This avoids the formation of junctions at the periphery of window component 18 which may be prone to break down and consequently permit ingress of fluids and the like from the surgical theater. Because the cover 140 functions as an electrical shield, the interior side surfaces thereof are made electrically conductive by the deposition thereof of a thin layer of gold as at 142. Finally, the external surface of the cover 140 preferably is coated with a polymeric low surface friction coating 144. This layer 144 may, for example, be provided as Teflon. The coating functions to aid in avoiding friction generated noise occasioned by the movement of the device over tissue and the implements typically encountered in a surgical theater.

Figure 4:
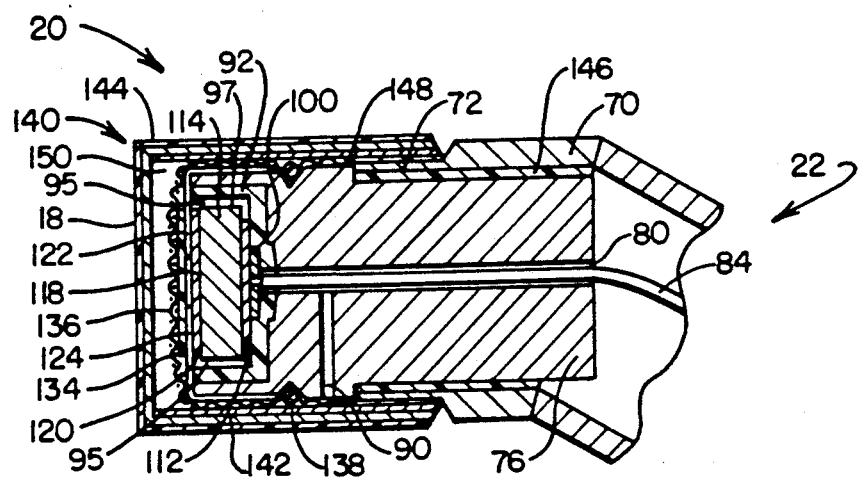
FIG. 4 is a sectional view of the forward portion of the instrument embodiment represented in FIG. 3.

Looking to FIG. 4, the final assembly of the instrument portion 20 is revealed in sectional detail. Note, that the retainer or slug 76 is adhesively coupled to supporting tubular portion 70 with a layer of electrically conductive epoxy cement 146, while the forward cover 140 additionally is retained over portion 72 of the housing by a conductive epoxy cement layer 148. Note in FIG. 4 that the assemblage of tubular portion 70, crystal 114, and the components associated therewith are so oriented upon final assembly that a dead space 150 is created between the forwardly-disposed surface 118 of crystal 114, as well as the associated cushioning, retainer, and electrical contact components, and the window portion 18 of cover 140. This dead air space provides an enhancement of acoustic isolation of the crystal 114.

As represented at circuit 44 in FIG. 2, in order to carry out the treatment of the very faint charges which are evolved due to gamma interaction with crystal 114, it is important that the preamplification function take place as close as possible to the situs of the interaction. In view of the operational need in surgery for the 30° cant of the central axis of the forward portion 20 with respect to the corresponding axis of the rearward support portion 22 of the probe 12, the small length of transmission wire 84 is required. Because extremely small charges of current age involved in the range of 300-600 atto-coulombs, a preamplification stage which performs to achieve a very high gain is called upon but one which performs with low noise generation. In effect, the preamplification stage of the instant apparatus is one achieving a voltage amplification, for example on the order of about 25,000.

Crystal 114 is maintained in a carefully electrically shielded, acoustically dead and light-tight environment. Aluminum cover 140 permits entry of very low level emissions of gamma radiation. Thus, the full forward face 118 of crystal 114 is exposed to radiation. Even though the window 18 portion of the cover 140 is relatively broad in extent, the capability of the instrument 12 to differentiate the interface between tissue carrying radiolabelled antibodies and the like and those not carrying these labels is quite accurate to the extent that collimation to achieve close differentiation typically is not required.

Figure 8:
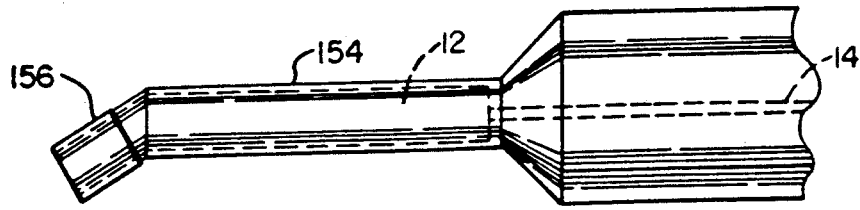
FIG. 8 is a side view of the probe instrument of FIG. 2 showing its employment with a sterile cover or sheath.

A technique which both simplifies cleaning the instrument and maintaining its sterile condition involves the use of a disposable plastic cover which fits over the probe device 12 and which is formed of a polymeric material which is readily produced in a sterile state. Thus, prior to an operation, the surgical personnel will slide the probe within the cover or sheath. The addition of the polymeric surface aids in the control of vibration induced noise as well as representing an ideal technique for maintaining the requisite sterile condition for the device. Looking to FIG. 8, the instrument 12 is shown in dashed line fashion with a polymeric cover 154. Cover 154 includes a nose portion 156 formed of a tough plastic having a thickness, for example, of 0.020 inch. This will protect the cover 154 from tearing or the like when used in the rigorous activities of surgery. From the nose portion 156 the sheath may extend rearwardly a sufficient length to cover the signal transmission components as at 14 for a sufficient distance to assure sterile integrity.

Figure 9A:
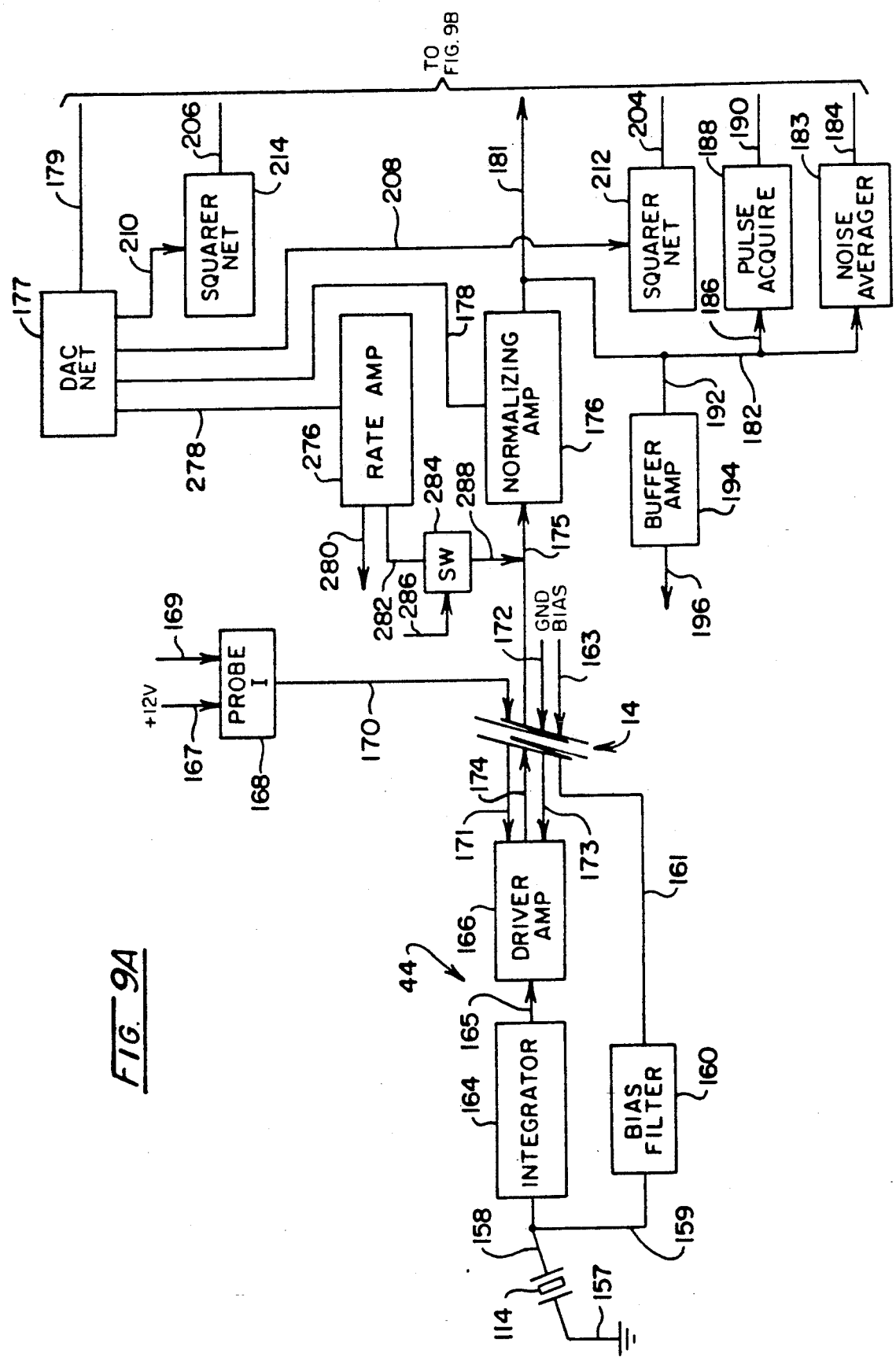

Referring to FIGS. 9A and 9B, a block diagrammatic representation of the instrumentation circuitry is revealed. In FIG. 9A, the cadmium telluride crystal 114 is shown having one face coupled to ground through line 157, while the opposite, biased face thereof is coupled via lines 158 and 159 to a bias filter represented at block 160. The input to the filter 160 is represented at line 161 as being applied through the triaxial cable as described earlier at 14 and represented by that numeral herein. Line 158 corresponds with the earlier-described line 62 in FIG. 2. This bias emanates from a power supply shown at block 162 in FIG. 9B and represented at line 163.

Line 158 from the crystal 114 is shown extending to an integrator stage 164 of the preamplifier 44. The integrated valuation of detected radiation disturbance then is shown directed as represented by line 165 to a drive-amplification network shown at block 166. A 12 v power supply is provided from the power supply 162 (FIG. 9B) as represented at line 167 which, as shown in FIG. 9A, is directed to a probe current network represented by block 168. Under microcomputer control as represented by line 169, the network 168 develops signals, for example, determining whether the probe instrument 12 has been properly connected to the console 16. Delivery of the 12 v power supply for the preamplifier stage 44 is represented at line 170 as extending to the drive amplifier from cable 14 via line 171. Line 171 corresponds with the clad 46 described in conjunction with cable 14 in FIG. 2.

Ground to the instrument 12 also is developed from the power supply block 162 as represented at line 172 shown in FIG. 9A as extending to cable 14 and via line 173 to the instrument preamplification components 44. Line 173 corresponds with the earlier-described clad at 48 in FIG. 2.

The output of the preamplification circuit 44 is represented at line 174 extending through the cable representation 14 corresponding with the earlier-described line 54 in FIG. 2. Line 174 extend from the cable 14 as line 175 to the input of a normalizing amplifier represented at block 176. The network represented by block 176 functions to amplify or attenuate, ie. scale the noise characteristic of any given instrument 12 and normalize the value thereof or render it consistent for layer comparison stages. Generally, for example the 27 kev energy level gamma ray generated pulses in the system will be about five times higher than noise levels. Normalizing amplifier network 176 will establish those noise levels at some predetermined level, for example, 200 millivolts and the resultant proportional valid gamma related pulses will become about one volt high for purposes of ensuing comparison functions. It may be observed that the amplifier network at block 176 is shown controlled from a digital-to-analog converter network represented at block 177 via line 178. Network 177, in turn, is controlled from line 179 extending, as shown in FIG. 9B, to block 180 representing a microcomputer network. The normalized output developed from network 176 is presented along lines 181 and 182 to a noise average circuit as represented at block 183. This network 183 determines in average amplitude value for the noise of a given system with a given instrument 12 and provides a corresponding signal as represented at line 184 (noise amp) which is employed as above-described as information used by the microcomputer 180. This information, in addition to being employed with the normalizing amplifier network represented at block 176 may be used to develop a low window valuation for the comparison function.

Line 182 also extends via line 186 to a pulse acquire network represented at block 188. This network functions, when activated by the microcomputer represented at block 180, to acquire the value of the highest pulse amplitude witnessed at line 186. Periodically, this information then is transmitted to the microcomputer at block 180 as represented by line 190. Representing a form of peak detector, the network is sometimes referred to as a "snapshot circuit". Also produced from line 182, as at line 192 and block 194 is a buffer amplifier which will provide at line 196 an output representing received pulses which may be made available at the rearward portion of console 16 for conventional radiation evaluation purposes.

Line 181 extends, as shown in FIG. 9B at line 198, to one input of an upper window comparator represented at block 200 and a lower window comparator illustrated at block 202. The threshold level for comparative purposes employed by the network at block 202 is shown asserted from line 204 and, preferably, is developed by the logic of microcomputer network 180 at a level just above the noise amplitude signals generated from line 184. Of course, manual setting of such windows can be carried, out. In similar fashion, the upper window of acceptance for valid gamma ray interaction is established from a corresponding line 206. This threshold setting may be made from the information taken from pulse acquire network 188.

Returning to FIG. 9A, the upper window and lower window threshold selections are made under the control of the microcomputer network at block 180 as controlled from the digital-to-analog network shown at block 177. It is the characteristic of such networks as at block 177 to provide an output which is comprised, for example, of 256 steps of varying amplitude. The percentage of incrementation from step-to-step will vary somewhat over the range of voltage values provided. Accordingly, the outputs from this conversion network at block 177, as at lines 208 and 210 are directed to squarer networks shown, respectively, at blocks 212 and 214. These networks function to square the current outputs at lines 208 and 210 and thus achieve a uniform percentage incrementation of the threshold defining outputs at lines 204 and 206.

Returning to FIG. 9B, the outputs of the comparator networks shown at blocks 200 and 202 represent candidate pulses which may be above or below the given thresholds and are identified as being presented as a "UW pulse" and an "LW pulse" along respective lines 216 and 218. These lines are shown directed to a real time pulse discriminator network represented at block 220 which carries out Boolean logic to determine the presence or absence of valid pulses. Valid pulses are introduced to the microcomputer network 180 as represented by line 222.

The microcomputer represented at block 180 performs under a number of operational modes to provide both audio and visual outputs to aid the surgeon in locating and differentiating tumorous tissue. In the former regard, as represented at line 224 and block 226, a volume control function may be asserted with amplitude variations controlled from a solid-state form of potentiometer as represented at line 228 and block 230. Further, a "siren" type of frequency variation may be asserted as represented at line 232 to an audio amplification circuit represented at block 234 for driving a speaker as represented at 236 and line 238. With the noted siren arrangement, the frequency output from speaker 236 increases as the instrument 12 is moved closer to the situs of concentrated radiation. Of course, conventional clicks and beeps can be provided at the option of the operator.

The microcomputer network 180, as represented by arrow 240 and block 242 also addresses an input-output network which, as represented at arrow 244, functions to provide a pulse count output of varying types as well as outputs represented volume levels, pulse height, noise levels and battery status. Visual readout is represented in FIG. 9B as a block with the same display 26 numeration as described in conjunction with FIG. 1. Similarly, the input-output function represented at block 242 provides appropriate scanning of the keyboard or switches described in conjunction with FIG. 1 at 30 and represented by the same numeration in FIG. 9B. During the counting operation, the microcomputer network 180 functions to control a light emitting diode drive network represented by block 246 from line 248. The drive network represented at block 246 is shown providing an input, as represented by line 250 to the dual LED display as described at 28 in FIG. 1 and represented in block form with the same numeration. This readout provides a red light when a gamma ray is detected and a green light during the counting procedure in general. A serial output port of conventional variety also is provided on the console 16, such ports being represented at block 252 being addressed from the microcomputer at block 180 from line 254 and having output and input components represented by arrow 256. A real time clock-calendar having a non-volatile memory also may be provided in conjunction with the functions of the microcomputer network 180 as represented by block 258 and arrow 260. Further, the microcomputer may be employed to monitor the performance of the power supply represented at block 162. This is shown being carried out by the interaction of the microcomputer network with a multiplexer represented at block 262 and having an association represented by arrows 264 and 266. It may be observed that the power supply also provides a +5 v source for the logic level components of the circuit as represented by line 268; a −5v source at line 270, as well as a −9v reference at line 272 for display 26 drive and, finally, a 2.5v reference as represented at line 274 to provide reference input tot he analog circuitry described later herein.

Returning to FIG. 9A, the microcomputer network as represented at block 180 also provides an input to the digital-to-analog conversion network represented at block 177 which corresponds with the instantaneous pulse rate and this information is conveyed to a pulse rate amplifier network represented at block 276 via line 278. The resultant output as represented at line 280 may be provided, for example, at the rear of the console 16. This circuit represented at block 276 also may be employed to generate a calibrating pulse for testing the downstream components of the system. Thus, the microcomputer applies a predetermined pulse level through the digital-to-analog conversion network at block 177 for presentation to the amplifier network represented at block 276. The resultant output at line 282 is selectively switched as represented by block 284 to define pulse width from the microcomputer input at line 286 to the calibrating pulse at line 288.

Since certain changes may be made in the above-described system and apparatus and method without departing from the scope of the invention herein involved, it is intended that all matter contained in the description thereof or shown in the accompanying drawings shall be interpreted as illustrative and not in a limiting sense.

I claim:

1. An instrument for detecting and locating sources of radiation emission having predetermined energy levels, comprising:

a housing having a forwardly disposed portion;

a crystal mount positioned within said housing forwardly disposed portion, formed of material attenuating radiation of said predetermined energy levels and having a forwardly disposed crystal receiving cavity having sidewalls extending inwardly thereinto from a forwardly disposed opening;

a resilient, electrically insulate polymeric layer within said cavity having an outwardly disposed electrically insulative surface;

a radiation responsive crystal located within said cavity having a rearwardly disposed surface positioned facing said electrically insulative surface and having a side portion extending to a forwardly disposed surface;

biasing means extending within said cavity and having a bias contact adjacent said electrically insulative surface;

a first electrically conductive compliant member conformable with and in contacting adjacency between said crystal rearwardly surface and said bias contact;

a second electrically conductive compliant member conformable with and in contacting adjacency with said crystal forwardly disposed surface;

grounding means positioned in abutting adjacency with said second compliant member for electrically grounding said crystal forwardly disposed surface;

resilient retainer means positioned in tension over said grounding means, said second electrically conductive compliant member and said crystal forwardly disposed surface for compressively retaining components including said grounding means and said second compliant member against said crystal forwardly disposed surface and said rearwardly disposed surface against said first compliant member, and bias contact, and said resilient polymeric layer to an extent effective to provide a stabilization of the electrical contacts to said crystal derived from said basing means and said grounding means and to retain said components in a statically stable state; and forward cover means positioned over and enclosing said crystal mount crystal receiving cavity, said crystal, said grounding means, and said resilient retainer means for permitting transmission of said radiation emission of said predetermined energy levels.

2. The instrument of claim 1 in which said electrical bias contact is in freely-abutting contact with said first electrically conductive compliant member.

3. The instrument of claim 1 in which said first electrically conductive compliant member is a carbon-filled non-woven polytetrafluoroethylene cloth.

4. The instrument of claim 1 in which said grounding means comprises an electrically conductive member extending over and in freely-abutting contact with said second electrically conductive compliant member.

5. The instrument of claim 1 in which said second electrically conductive compliant member is a carbon-filled, non-woven polytetrafluoroethylene cloth.

6. The instrument of claim 1 including a polymeric, low surface friction coating located over the outwardly disposed surface of said forward cover means.

7. The instrument of claim 1 including a disposable, sterile, thin polymeric cover positionable over said instrument for isolating the components thereof from contaminants and presenting a sterile instrument exterior for surgical utilization.

8. The instrument of claim 1 in which:
said grounding means comprises a wire lead electrically coupled with said housing and extending over and in freely-abutting contact with said second electrically conductive compliant member.

9. The instrument of claim 1 in which said grounding means comprises a wire lead fixed to and supported from said crystal mount and extending over and in freely-abutting contact with said second electrically conductive compliant member.

10. The instrument of claim 1 in which said resilient retainer means is a resilient web positioned in tension over said second electrically conductive compliant member and fixed in tension to said crystal mount.

11. The instrument of claim 1 in which said crystal mount crystal receiving cavity is configured having a depth at least coextensive with said crystal side portion so as to attenuate radiation otherwise incident thereon.

12. The instrument of claim 1 in which:
said bias contact is in freely-abutting contact with said first electrically conductive compliant member;
said grounding means comprises an electrically conductive member extending over and in freely-abutting contact with said second electrically conductive compliant member; and
said resilient retainer means is a resilient web positioned in tension over said grounding means and fixed to said crystal mount so as to effect a compressive retention of said grounding means against said second compliant member and said second compliant member against said crystal forwardly disposed surface.

13. The instrument of claim 12 in which said first and second electrically compliant members are carbon-filled, non-woven polytetrafluoroethylene cloth.

14. The instrument of claim 13 in which said resilient retainer means is a nylon web.

15. An instrument for detecting sources of radiation emissions, comprising:
a housing having a forwardly disposed portion;
a crystal mount positioned within said housing forwardly disposed portion having an electrically insulative forwardly disposed crystal supporting surface;
a radiation responsive crystal having a rearwardly disposed surface positioned facing said crystal mount crystal supporting surface and having a side portion extending to a forwardly disposed surface;
electrical biasing means having a bias contact at said crystal mount crystal supporting surface;
a first electrically conductive compliant cushioning member conformable with and in contacting adjacency between said crystal rearwardly disposed surface and said bias contact;
a second electrically conductive compliant cushioning member conformable with and in contacting adjacency with said crystal forwardly disposed surface;
grounding means positioned in adjacency with said second compliant member for electrically grounding said crystal forwardly disposed surface by electrical association therewith through said second compliant member;
a resilient web retainer positioned in tension over said grounding means and said second electrically conductive compliant cushioning member for compressibly retaining components including said grounding means, said second electrically conductive compliant cushioning member, and said crystal and said first electrically conductive compliant cushioning member upon said crystal mount supporting surface to an extent effective to provide a stabilization of the electrical contacts to said crystal derived from said biasing means and said grounding means and to retain said components in a statically stable state; and
a forward cover positioned over and in enclosing relationship with said crystal mount crystal supporting surface, said crystal, said grounding means, and said first and second electrically conductive compliant cushioning members for excluding external contaminants, and having a forwardly disposed window portion formed of material permitting substantial transmission of said radiation emissions to said crystal forwardly disposed surface, said window portion being spaced forwardly from said crystal to define a dead air space for enhancing the acoustic isolation of said crystal.

16. The instrument of claim 15 in which said crystal mount crystal supporting surface is within a crystal receiving cavity having sidewalls spaced from said crystal side portion to define a gap therebetween of dimension effective to avoid the generation of electrical noise phenomena, said crystal receiving cavity being configured a depth at least coextensive with said crystal side portion so as to attenuate radiation otherwise incident thereon.

17. The instrument of claim 15 in which said electrical biasing means is in freely abutting contact with said first electrically conductive compliant cushioning member.

18. The instrument of claim 15 in which said grounding means comprises an electrically conductive wire member extending over and in freely abutting contact with said second electrically conductive compliant cushioning member.

19. The instrument of claim 15 in which said first electrically conductive compliant cushioning member is a carbon-filled non-woven polytetrafluoroethylene cloth.

20. The instrument of claim 15 in which said second electrically conductive compliant cushioning member is a carbon-filled non-woven polytetrafluoroethylene cloth.

21. The instrument of claim 15 including a disposable, sterile, thin polymeric cover positionable over said instrument for isolating the components thereof from contaminants and presenting a sterile instrument exterior for surgical utilization.

22. The instrument of claim 15 in which said resilient retainer web is fixed in tension to said crystal mount.

23. The instrument of claim 15 in which said resilient retainer is a nylon web.

24. An instrument for detecting sources of gamma radiation emissions, comprising:
a housing having a forwardly disposed portion;
a crystal mount positioned within said housing forwardly disposed portion having an electrically insulative, forwardly disposed crystal supporting surface;
a gamma radiation responsive crystal having a rearwardly disposed surface positioned facing said crystal mount crystal supporting surface and having a side surface extending to a forwardly disposed surface;

compliant cushioning means for locating said cyrstal upon said crystal supporting surface with substantial immunity from externally induced vibration phenomena;

electrical biasing means for applying an electrical bias to said crystal rearwardly disposed surface;

grounding means for electrically grounding said crystal forwardly disposed surface;

a resilient web retainer positioned in tension over and compressively retaining components including said gamma radiation responsive crystal, said compliant cushioning means, said electrical biasing means and said grounding means for effecting the retention thereof in compression upon said crystal mount crystal supporting surface to an extent effective to provide a stabilization of electrical contacts to the crystal derived from said biasing means and said grounding means and to retain said components in a statically stable state; and a foward cover positioned over and in enclosing relationship with said crystal mount crystal supporting surface, said crystal, said compliant cushioning means, and said grounding means for excluding external contaminants, and having a forwardly disposed window portion formed of material permitting substantial transmission of said gamma radiation to said crystal forwardly disposed surface, said window portion being spaced forwardly from said crystal to define a space enhancing the isolation of said crystal from externally induced vibration phenomena.

25. The instrument of claim 24 in which:
said compliant cushioning means is electrically conductive; and
said grounding means is configured to assert ground to said crystal forwardly disposed surface through said compliant cushioning means.

26. The instrument of claim 24 in which:
said compliant cushioning means is electrically conductive; and
said electrical biasing means is configured to apply said electrical bias to said crystal rearwardly disposed surface through said compliant cushioning means.

27. The instrument of claim 24 including a disposable, sterile, thin polymeric cover positionable over said instrument for isolating the components thereof from contaminants and presenting a sterile instrument exterior for surgical utilization.

28. The instrument of claim 24 in which said resilient retainer means is a nylon web.

29. The instrument of claim 24 in which said compliant cushioning means is a carbon-filled, non-woven polytetrafluoroethylene cloth.

30. An instrument for detecting and locating sources of radiation emission having predetermined energy levels, comprising:

a housing having a forwardly disposed portion;

a crystal mount positioned within said housing forwardly disposed portion, formed of material attenuating radiation of said predetermined energy levels and having a forwardly disposed crystal receiving cavity having a sidewall extending inwardly thereinto to an electrically insulative surface from a forwardly disposed opening.

a radiation responsive crystal located within said cavity having a rearwardly disposed surface positioned facing said electrically insulative surface and having a side portion extending to a forwardly disposed surface, said crystal side portion being spaced from said crystal receiving cavity sidewall a distance selected to effect a substantially non-contacting relationship therebetween;

biasing means extending within said cavity and having a bias contact adjacent said electrically insulative surface;

a first electrically conductive compliant member conformable with and in contacting adjacency between said crystal rearwardly disposed surface and said bias contact;

a second electrically conductive compliant member conformable with and in contacting adjacency with said crystal forwardly disposed surface;

grounding means positioned in abutting adjacency with said second compliant member for electrically ground said crystal forwardly disposed surface;

resilient retainer means positioned in tension over said grounding means, said second electrically conductive compliant member and said crystal forwardly disposed surface for compressively retaining said grounding means and said second compliant member against said crystal forwardly disposed surface and said rearwardly disposed surface against said first compliant member and said bias contact; and forward cover means positioned over and enclosing said crystal mount, said crystal, said grounding means, and said resilient means for permitting transmission of said radiation emission of said predetermined energy levels.

31. The instrument of claim 30 in which said radiation responsive crystal side portion is spaced from said crystal receiving cavity sidewall a distance of about 0.005 inch.

32. The instrument of claim 30 including a disposable, sterile, thin polymeric cover positionable over said instrument for isolating the components thereof from contaminants and presenting a sterile instrument exterior for surgical utilization.

33. An instrument for detecting and locating sources of radiation emission having predetermined energy levels, comprising:

a housing having a forwardly disposed portion;

a crystal mount positioned within said housing forwardly disposed portion, formed of material attenuating radiation of said predetermined energy levels and having a forwardly disposed crystal receiving cavity having a sidewall extending thereinto to an electrically insulative surface from a forwardly disposed opening;

a radiation responsive crystal located within said cavity having a rearwardly disposed surface positioned facing said electrically insulative surface and having a side portion extending to a forwardly disposed surface, said crystal side portion being spaced from said crystal receiving cavity sidewall to define a gap therebetween effective to avoid the generation of electrical noise phenomena;

biasing means extending within said cavity and having a bias contact adjacent said electrically insulative surface;

a first electrically conductive compliant member conformable with and in contacting adjacency between said crystal rearwardly disposed surface and said bias contact;

a second electrically conductive compliant member conformable with and in contacting adjacency with said crystal forwardly disposed surface;

grounding means positioned in abutting adjacency with said second compliant member for electrically grounding said crystal forwardly disposed surface;

resilient retainer means positioned in tension over said grounding means, said second electrically conductive compliant member and said crystal forwardly disposed surface for compressively retaining said grounding means and said second compliant member against said crystal forwardly disposed surface and said rearwardly disposed surface against said first compliant member and said bias contact; and forward cover means positioned over and enclosing said crystal mount, said crystal, said grounding means, and said resilient retainer means for permitting transmission of said radiation emissions of said predetermined energy levels.

34. An instrument for detecting sources of radiation emissions, comprising:

a housing having a forwardly disposed portion;

a crystal mount positioned within said housing forwardly disposed portion having a crystal receiving cavity with a sidewall extending inwardly thereinto to an electrically insulative forwardly disposed crystal supporting surface;

a radiation responsive crystal having a rearwardly disposed surface positioned facing said crystal mount crystal supporting surface and having a side portion extending to a forwardly disposed surface, said crystal side portion being spaced from said crystal receiving cavity sidewall to define a gap therebetween of dimension effective to avoid generation of noise phenomena;

electrical biasing means having a bias contact at said crystal mount crystal supporting surface;

a first electrically conductive compliant cushioning member conformable with and in contacting adjacency between said crystal rearwardly disposed surface and said bias contact; and a second electrically conductive compliant cushioning member conformable with and in contacting adjacency between said crystal forwardly disposed surface;

grounding means positioned in adjacency with said second compliant member for electrically grounding said crystal forwardly disposed surface;

resilient retainer means positioned in tension over said second electrically conductive compliant cushioning member for compressibly retaining said second electrically conductive compliant cushioning member, said crystal and said first electrically conductive compliant cushioning member upon said crystal mount supporting surface; and a forward cover positioned over and in enclosing relationship with said crystal mount crystal supporting surface, said crystal, and said first and second electrically compliant cushioning members for excluding external contaminants, and having a forwardly disposed window portion formed of material permitting substantial transmission of said radiation emissions to said crystal forwardly disposed surface, said window portion being spaced forwardly from said crystal to define a dead air space for enhancing the acoustic isolation of said crystal.

35. An instrument for detecting sources of gamma radiation emissions, comprising:

a housing having a forwardly disposed portion;

a crystal mount positioned within said housing forwardly disposed portion having a crystal receiving cavity with a sidewall extending inwardly thereinto to an electrically insulative, forwardly disposed crystal supporting surface.

a gamma radiation responsive crystal having a rearwardly disposed surface positioned facing said crystal mount crystal supporting surface and having a side surface extending to a forwardly disposed surface, said crystal side surfaces being spaced from said crystal receiving cavity sidewall to define a gap therebetween of dimension effective to avoid the generation of noise phenomena;

compliant cushioning means for locating said crystal upon said crystal supporting surface with substantial immunity from externally induced vibration phenomena;

electrical biasing means for applying an electrical bias to said crystal rearwardly disposed surface;

grounding means for electrically grounding said crystal forwardly disposed surface;

resilient retainer means positioned in tension over said gamma radiation responsive crystal, said compliant cushioning means, said electrical biasing means and said grounding means for effecting the retention thereof in compression upon said crystal mount crystal supporting surface; and a forward cover positioned over and in enclosing relationship with said crystal mount crystal supporting surface, said crystal, said compliant cushioning means, and said grounding means for excluding external contaminants, and having a forwardly disposed window portion formed of material permitting substantial transmission of said gamma radiation to said crystal forwardly disposed surface, said window portion being spaced forwardly from said crystal to define a space enhancing the isolation of said crystal from externally induced vibration phenomena.

36. An instrument for detecting and locating sources of radiation emission having predetermined energy levels, comprising:

a housing having a forwardly disposed portion;

a crystal mount positioned within said housing forwardly disposed portion, formed of material attenuating radiation of said predetermined energy levels and having a forwardly disposed crystal receiving cavity having a sidewall extending inwardly thereinto to an electrically insulative surface from a forwardly disposed opening.

a radiation responsive crystal located within said cavity having a rearwardly disposed surface positioned facing said electrically insulative surface and having a side portion extending to a forwardly disposed surface, said crystal side portion being spaced from said crystal receiving cavity sidewall a distance of about 0.005 inch;

biasing means extending within said cavity and having a bias contact adjacent said electrically insulative surface;

a first electrically conductive compliant member conformable with and in contacting adjacency between said crystal rearwardly disposed surface and said bais contact;

a second electrically conductive compliant member conformable with and in contacting adjacency with said crystal forwardly disposed surface;

grounding means positioned in abutting adjacency with said second compliant member for electrically grounding said crystal forwardly disposed surface;

resilient retainer means positioned in tension over said grounding means, said second electrically conductive compliant member and said crystal forwardly disposed surface for compressively retaining said grounding means and said second compliant member against said crystal forwardly disposed surface and said rearwardly disposed surface against said first compliant member and said bais contact; and forward cover means positioned over and enclosing said crystal mount, said crystal, said grounding means, and said resilient retainer means for permitting transmission of said radiation emission of said predetermined energy levels.

37. An instrument for detecting and locating sources of radiation emission having predetermined energy levels comprising:

a housing having a forwardly disposed portion;

a crystal mount positioned within said housing forwardly disposed portion, formed of material attenuating radiation of said predetermined energy levels and having a forwardly disposed crystal receiving cavity having sidewalls extending inwardly thereinto from a forwardly disposed opening;

a pliant, electrically insulative and cushioning polymeric layer within said cavity having an outwardly disposed electrically insulative surface;

a radiation responsive crystal located within said cavity having a rearwardly disposed surface positioned facing said electrically insulative surface and having a side portion extending to a forwardly disposed surface;

biasing means extending within said cavity and having a bias contact adjacent said electrically insulative surface;

a first electrically conductive compliant member conformable with and in contacting adjacency between said crystal rearwardly disposed surface and said bais contact;

a second electrically conductive compliant member conformable with and in contacting adjacency with said crystal forwardly disposed surface;

at least one thin grounding wire electrically coupled with said housing and extending over and in freely abutting contact with said second electrically conductive compliant member.

a resilient retainer web positioned in tension over said grounding means, said second electrically conductive compliant member and said crystal forwardly disposed surface for compressively retaining components including said grounding wire and said second compliant member against said crystal forwardly disposed surface and said rearwardly disposed surface against said first compliant member, said bais contact, and said resilient polymeric layer to an extent effective to provide a stabilization of the electrical contacts to said crystal derived from said biasing means and said grounding means and to retain said components in a statically stable state; and forward cover means positioned over and enclosing said cyrstal mount crystal receiving cavity, said crystal, said grounding wire and said resilient retainer web for permitting transmission of said radiation emission of said predetermined energy levels.

38. An instrument for detecting sources of gamma radiation emissions, comprising:

a housing having a forwardly disposed portion;

a crystal mount positioned within said housing forwardly disposed portion having an electrically insulative, forwardly disposed crystal supporting surface;

a gamma radiation responsive crystal having a rearwardly disposed surface positioned facing said crystal mount crystal supporting surface and having a side surface extending to a forwardly disposed surface;

compliant cushioning means for locating said crystal upon said crystal supporting surface with substantially immunity from externally induced vibration phenomena;

electrical biasing means for applying an electrical bias to said crystal rearwardly disposed surface;

a resilient nylon web retainer positioned in tension over and compressively retaining components including said gamma radiation responsive crystal, said compliant cushioning means, said electrical biasing means and said grounding means for effecting the retention thereof in compression upon said crystal mount crystal supporting surface to an extent effective to provide a stabilization of electrical contacts to the crystal derived from said biasing means and said grounding means and to retain said components in a statically stable state; and a forward cover positioned over and in enclosing relationship with said crystal mount crystal supporting surface, said crystal, said compliant cushioning means, and said grounding means for excluding external contaminants, and having a forwardly disposed window portion formed of material permitting substantial transmission of said gamma radiation to said crystal forwardly disposed surface, said window portion being spaced forwardly from said crystal to define a space enhancing the isolation of said crystal from externally induced vibration phenomena.

39. An instrument for detecting sources of radiation emissions, comprising:

a housing having a forwardly disposed portion;

a crystal mount positioned within said housing forwardly disposed portion having an electrically insulative forwardly disposed crystal supporting surface;

a radiation responsive crystal having a rearwardly disposed surface positioned facing said crystal mount supporting surface and having a side portion extending to a forwardly disposed surface;

electrical biasing means having a bias contact at said crystal mount supporting surface;

a first electrically conductive compliant cushioning member conformable with and in contacting adjacency between said crystal rearwardly disposed surface and said bias contact;

a second electrically conductive compliant cushioning member conformable with and in contacting adjacency with said crystal forwardly disposed surface;

a plurality of thin grounding wires positioned in adjacency with said second compliant member for electrically grounding said crystal forwardly disposed surface by electrical association therewith through said second compliant member.

a resilient web retainer positioned in tension over said grounding wires and said second electrically conductive compliant cushioning member for compressibly retaining components including said grounding wires, said second electrically conductive compliant cushioning member, and said crystal and said first electrically conductive compliant cushioning member upon said crystal mount supporting surface to an extent effective to provide a stabilization of the electrical contacts to said crystal derived from said biasing means and said grounding wires and to retain said components in a statically stable state; and a forward cover positioned over and in enclosing relationship with said crystal mount crystal supporting surface, said crystal, said grounding wires, and said first and second electrically conductive compliant cushioning members for excluding external contaminants, and having a forwardly disposed window portion formed of material permitting substantial transmission of said radiation emissions to said crystal forwardly disposed surface, said window portion being spaced forwardly from said crystal to define a dead air space for enhancing the acoustic isolation of said crystal.

40. An instrument for detecting and locating sources of radiation emission having predetermined energy levels, comprising:

a housing having a forwardly disposed portion;

a crystal mount positioned within said housing forwardly disposed portion, formed of material attenuating radiation of said predetermined energy levels and having a forwardly disposed crystal receiving cavity having sidewalls extending inwardly thereinto from a forwardly disposed opening;

a resilient, electrically insulative and cushioning polymeric layer within said cavity having an outwardly disposed electrically insulative surface;

a radiation responsive crystal located within said cavity having a rearwardly disposed surface positioned facing said electrically insulative surface and having a side portion extending to a forwardly disposed surface;

biasing means extending within said cavity and having a bias contact adjacent said electrically insulative surface;

a first electrically conductive compliant member formed of carbon-filled, non-woven polytetrafluoroethylene cloth conformable with and in contacting adjacency between said crystal rearwardly disposed surface and said bias contact;

a second electrically conductive compliant member formed of carbon-filled, non-wove polytetrafluoroethylene cloth conformable with and in contacting adjacency with said crystal forwardly disposed surface;

grounding means positioned in abutting adjacency over said second compliant member for electrically grounding said crystal forwardly disposed surface;

resilient retainer means positioned in tension over said grounding means, said second electrically conductive compliant member and said crystal forwardly disposed surface for compressively retaining components including said grounding means and said second compliant member against said crystal forwardly disposed surface and said rearwardly disposed surface against said first compliant member, said bias contact, and said resilient polymeric layer to an extent effective to provide a stabilization of the electrical contacts to said crystal derived from said biasing means and said grounding means and to retain said components in a statically stable state; and forward cover means positioned over and enclosing said crystal mount crystal receiving cavity, said crystal, said grounding means, and said resilient retainer means for permitting transmission of said radiation emission of said predetermined energy levels.

* * * * *